(12) United States Patent
Freyberg et al.

(10) Patent No.: US 9,017,693 B2
(45) Date of Patent: Apr. 28, 2015

(54) APOPTOTICALLY ACTIVE PEPTIDES

(75) Inventors: Mark A. Freyberg, Darmstadt (DE); Peter Friedl, Gross-Umstadt (DE); Dirk Kaiser, Eppertshausen (DE)

(73) Assignee: Cytotools AG, Darmstadt (DE)

( * ) Notice: Subject to any disclaimer, the term of this patent is extended or adjusted under 35 U.S.C. 154(b) by 805 days.

(21) Appl. No.: 12/977,672

(22) Filed: Dec. 23, 2010

(65) Prior Publication Data

US 2011/0178000 A1    Jul. 21, 2011

Related U.S. Application Data

(62) Division of application No. 10/499,930, filed as application No. PCT/EP02/14439 on Dec. 18, 2002, now Pat. No. 7,892,556.

(30) Foreign Application Priority Data

Dec. 20, 2001    (DE) .................................. 101 63 130

(51) Int. Cl.
*A61K 38/00* (2006.01)
*A61K 38/04* (2006.01)
*C07K 14/47* (2006.01)

(52) U.S. Cl.
CPC ............. *C07K 14/4747* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,479,930 A | 10/1984 | Hnatowich | |
| 4,652,440 A | 3/1987 | Paik et al. | |
| 4,668,503 A | 5/1987 | Hnatowich | |
| 5,399,667 A | 3/1995 | Frazier et al. | |
| 5,627,048 A * | 5/1997 | Afanasiev et al. | 435/69.1 |
| 6,166,178 A * | 12/2000 | Cech et al. | 530/324 |
| 2004/0123343 A1 * | 6/2004 | La Rosa et al. | 800/278 |

FOREIGN PATENT DOCUMENTS

| | | |
|---|---|---|
| WO | WO-96/11942 A1 | 4/1996 |
| WO | WO-96/17059 A2 | 6/1996 |
| WO | WO-96/17059 A3 | 6/1996 |
| WO | WO-00/45856 A2 | 8/2000 |
| WO | WO-00/45856 A3 | 8/2000 |
| WO | WO-00/47102 A2 | 8/2000 |

OTHER PUBLICATIONS

Gotschlick et al The DNA Sequence of the Structural Gene of Gonococcal Protein III and the Flanking Region Containing a Repetitive Sequence Homology of Protein III with Enterobacterial OmpA Proteins. (J. Exp. Med. 165, 471-482, 1987).*
Curtis et al. Algal genomes reveal evolutionary mosaicism and the fate of nucleomorphs. Nature 492:59-65(2012).*
Kawarabayasi et al. Complete Genome Sequence of an Aerobic Hyper-thermophilic Crenarchaeon, Aeropyrum pernixKI. (DNA Res. 6, 83-101, 1999).*
Parkhill et al. Complete DNA sequence of a serogroup A strain of *Neisseria meningitidis* Z2491. Nature 404, 502-506, 2000.*
Leon et al. Sequencing, annotation, and characterization of the influenza ferret infectome. J. Virol. 87:1957-1966(2013).*
Adams et al., Extracellular matrix retention of thrombospondin 1 is controlled by its conserved C-terminal region. *J. Cell Sci.* 121(Pt 6):784-95 (2008).
Adang et al., Case histories of peptidominetics: Progression from peptides to drugs. *Recueil des Travaux Chimiques des Pays-Bas*, 113: 63-78 (1994).
Aina et al., Therapeutic cancer targeting peptides. *Biopolymers*, 66(3): 184-99 (2002).
Anilkumar et al., Trimeric assembly of the C-terminal region of thrombospondin-1 or thrombospondin-2 is necessary for cell spreading and fascin spike organization. *J. Cell Sci.* 115(Pt 11): 2357-66 (2002).
Aoudjit et al., Matrix attachment regulates Fas-induced apoptosis in endothelial cells: a role for c-flip and implications for anoikis. *J. Cell Biol.* 152(3):633-43 (2001).
Armstrong et al., Thrombospondins 1 and 2 function as inhibitors of angiogenesis. *Matrix Biology*, 22(1):63-71 (2003).
Asai et al., Peripheral vascular endothelial dysfunction and apoptosis in old monkeys. *Arterioscler. Thromb. Vasc. Biol.* 20(6):1493-9 (2000).
Blackwell et al., Ring-closing metathesis of olefinic peptides: Design, synthesis, and structural characterization of macrocyclic helical peptides. *J. Org. Chem.* 66:5291-302, © 2001 American Chemical Society.
Borchardt, Optimizing oral absorption of peptides using prodrug strategies. *J. Control. Release*, 62: 31-8 (1999).
Bornstein, Thrombospondins as matricellular modulators of cell function. *J. Clin. Invest.* 107(8): 929-34 (2001).
Carron et al., A CD36-binding peptide from thrombospondin-1 can stimulate resorption by osteoclasts in vitro. *Biochem. Biophys. Res. Commun.* 270: 1124-7 (2000).
Cohen, Apoptosis, *Immunol. Today*, 14(3):126-36 (1993).
Darzynkiewicz et.al ., Features of apoptotic cells measured by flow cytometry, *Cytometry*, 13: 795-808 (1992).
DeKroon et al., ApoE genotype-specific inhibition of apoptosis. *J. Lipid Res.* 44(8): 1566-73 (2003).
Fan et al., Inflammatory reactions in the pathogenesis of atherosclerosis. *J. Atheroscler. Thromb.* 10(2): 63-71 (2003).
Feldmann et al., Database Genbank Online, Complete DNA sequence of yeast chromosome II, Mar. 11, 1998.
Fleischmann et al., Database Genbank Online, Metabolism and evolution of *Haemophilus influenzae* deduced from a whole-genome comparison with *Escherichia coli*, May 29, 1998.
Freyberg et al., Integrin-associated protein and thrombospondin-1 as endothelial mechanosensitive death mediator. *Biochem. Biophys. Res. Commun.* 271(3): 584-8 (2000).

(Continued)

*Primary Examiner* — Maher Haddad
(74) *Attorney, Agent, or Firm* — Marshall, Gerstein & Borun LLP

(57) ABSTRACT

Specific amino acid sequences and peptides and/or peptide mimetics deducted therefrom influencing apoptosis, and the use thereof for the production of pharmaceuticals as diagnostic tools are shown.

5 Claims, No Drawings

(56) References Cited

OTHER PUBLICATIONS

Freyberg et al., Proantherogenic flow conditions initiate endothelial apoptosis via thrombospondin-1 and the integrin-associated protein. *Biochem. Biophys. Res. Commun.* 286: 141-9 (2001).
Friedberg et al., Database Genbank Online, The amino acid sequence of Lrp is highly conserved in four enteric microorganisms, Sep. 19, 1995.
Gante, Peptidmimetica—MaBgeschneiderte Enzymithibitoren, *Angew. Chem.* 106: 1780-802 (1994).
Gao et al., Integrin-associate protein in a receptor for the C-terminal domain of thrombospondin. *J. Biol. Chem.* 271(1): 21-4 (1996).
Gao et al., Thrombospondin modulates $ct,\alpha_v\beta_3$ function through integrin-associated protein. *J. Call Biol.* 135(2): 533-44 (1996).
Genbank Accession No. AY069650, *Drosophila melanogaster* LD 41918 full length cDNA, submitted Dec. 10, 2001.
Graf et al., A common mechanism for the mechanosensitive regulation of apoptosis in different cell types and for different mechanical stimuli. *Apoptosis*, 8(5): 531-8 (2003).
Gruber et al., The human antimouse immunoglobulin response and the anti-idiotypic network have no influence on clinical outcome in patients with minimal residual colorectal cancer treated with monoclonal antibody CO17-1A. *Cancer Res.* 60(7): 1921-6 (2000).
Hartmann et al., Database Genbank Online, *Drosophila melanogaster* RanBP11, Jun. 1, 2000.
Hogg et al., Thrombospondin is a tight-binding competitive inhibitor of neutrophil elastase. *J. Biol. Chem.* 268(10): 7139-46 (1993).
Jimenez et al., Signals leading to apoptosis-dependent inhibition of neovascularization by thrombospondin-1, *Nat. Med.* 6(1):41-8 (2000).
Kosfeld et al., Identification of a new cell adhesion motif in two homologous peptides from the COOH-terminal cell binding domain of human thrombospondin. *J. Biol. Chem.* 268(12): 8808-14 (1993).
Kuznetsova et al., Functional regulation of T lymphocytes by modulatory extracellular matrix proteins. *Int. J. Biochem. Cell Biol.* 36(6): 1126-34 (2004).
Kvansakul et al., Structure of a thrombospondin C-terminal fragment reveals a novel calcium core in the type 3 repeats. *EMBO J.* 23(6): 1223-33 (2004).
Lee et al., Database Genbank Online, Molecular cloning, chromosomal mapping, and sequence analysis of copper resistance genes from *Xanthomonas campestris* PV juglandis: Homology with small blue copper proteins and multicopper oxidase, Mar. 17, 1994.
Lee et al., Database Genbank Online, Multidrug resistance genes are silent in streptomyces, Nov. 3, 2001.
Mateo et al., Mechanisms of CD47-induced caspase-independent cell death in normal and leukemic cells: link between phosphatidylserine exposure and cytoskeleton organization. *Blood*, 100(8): 2882-90 (2002).
Moodley et al., Macrophage recognition and phagocytosis of apoptotic fibroblasts is critically dependent on fibroblast-derived thrombospondin 1 and CD36. *Am. J. Pathol.* 162(3): 771-9 (2003).
Nakajima, Database Genbank Online, *Pseudomonas syringae* PV actinidiae copper resistance genes, Jun. 3, 2000.
Nofer et al., Suppression of endothelial cell apoptosis by high density lipoproteins (HDL) and HDL-assoicated lysosphingolipids. *J. Biol. Chem.* 276(37): 34480-5 (2001).
Primo et al., Identification of CD36 molecular features required for its in vitro angiostatic activity. *FASEB J.* 19(12): 1713-5 (2005).
Rath et al., The C-terminal CD47/IAP-binding domain of thrombospondin-1 prevents camptothecin- and doxorubicin-induced apoptosis in human thyroid carcinoma cells. *Biochim Biophys Acta.*, 1763(10):1125-34 (2006).
Read et al., Database Genbank Online, The genome sequence of *Bacillus anthracis* ames and comparison to closely-related bacteria, Apr. 30, 2003.
Savill et al., Thrombospondin cooperates with CD36 and the vitronectin receptor in macrophage recognition of neutrophils undergoing apoptosis. *J. Clin. Invest.* 90(4): 1513-22 (1992).
Skeiky et al., Database Genbank Online, Propionibacterium acnes polypeptides and nucleic acids useful for vaccinating against and diagnosing infections, especially useful for treating acne vulgaris, Nov. 1, 2001.
Stapleton et al., Database Genbank Online, *Drosophila melanogaster* LD41918 full length cDNA fruit fly, Dec. 17, 2001.
Staton et al., Current methods for assaying angiogenesis in vitro and in vivo. *Int. J. Exp. Pathol.* 85(5):233-48 (2004).
Swerlick et al., Human dermal microvascular endothelial but not human umbilical vein endothelial cells express CD36 in vivo and in vitro. *J. Immunol.* 148(1): 78-83 (1992).
Tettelin et al., Database Genbank Online, Complete genome sequence of *Neisseria meningitidis* serogroup B strain MC58, May 25, 2000.
Tricot et al., Relation between endothelial cell apoptosis and blood flow direction in human atherosclerotic plaques. *Circulation*, 101(21): 2450-3 (2000).
Xu et al., Computational tools for protein modeling. *Curr. Protein Pept. Sci.* 1(1):1-21 (2000).
Yao et al., A triple altered collagen II peptide with conservative substitutions of TCR contacting redisues inhibits collagen-induced arthritic. *Ann. Rheum. Dis.* 66(3): 423-4 (2007).
Yokyama et al., Improved biological activity of a mutant endostatin containing a single amino-acid substitution. *Br. J. Cancer*, 90:1627-35 (2004).
Zamai et al., Optimal detection of apoptosis by flow cytometry depends on cell morphology. *Cytometry*, 14: 891-7 (1993).
Zhou et al., Thrombospondin 1 mediates angiotensin II induction of TGF-beta activation by cardiac and renal cells under both high and low glucose conditions. *Biochem. Biophys. Res. Commun.* 339(2): 633-41 (2006).
Communication from European Patent Office in Application No. 02 805 332.0-2406, dated Feb. 4, 2009.
International Search Report in PCT/EP02/14439 dated Aug. 4, 2003.

\* cited by examiner

APOPTOTICALLY ACTIVE PEPTIDES

This application is a divisional of U.S. patent application Ser. No. 10/499,930, filed Jun. 6, 2005, now U.S. Pat. No. 7,892,556, issued Feb. 22, 2011, which is the U.S. national phase of International Application No. PCT/EP02/14439 filed Dec. 18, 2002, the entire disclosures of which are incorporated herein by reference.

BACKGROUND OF THE DISCLOSURE

1. Field of the Disclosure

The disclosure relates to apoptotically active peptides and the use thereof for the production of pharmaceuticals.

2. Related Technology

Apoptosis is a genetically encoded suicide program which under particular physiologic or pathologic conditions is induced in eucaryote cells. The induction of apoptosis has to be controlled extremely precisely since hyperactivity can lead to degenerative disorders. Reduced apoptosis induction, on the other hand, can contribute to tumor progression.

Various low-molecular inductors of apoptosis have already been described. A significant class are tumor cytostatica. In most of the cases, it is, however, not clear in which way these cytostatica or other substances can induce apoptosis.

Induction of apoptosis can for instance result via a series of so-called death receptors, i.e. receptors including a "Death Domain" (DD) such as CD95, TNF-RI, DR3, DR4 or DR5, which after binding of their ligands induce apoptosis signal ways. The CD95 receptor, for instance, interacts after binding of the CD95 ligand with the adapter protein FADD/MORT1 whereby "recruitment" and activation of the protease FLICE/CASpase-8 are induced at the DISC, the "Death Inducing Signaling Complex". FADD and FLICE each include "Death Effector Domains" (DED). Induction of apopotsis from outside via these signal ways is possible for instance by the addition of cell poisons (cytotoxic substances), by irradiation, viruses, withdrawal of growth factors or mechanical cell injure. These possibilities of apoptosis induction, however, are accompanied by special disadvantages. Addition of cell poisons, such as cytostatica, or irradiation in case of cancer cells leads to resistance development and, moreover, to damage of normal cells in which, originally, no apoptosis was to be triggered.

In general, induction of apoptosis is suggested for instance for the treatment of cancer, for avoiding angio-genetic processes etc. While inductors have here been described they still have a series of disadvantages. Cytostatica for instance generate heavy side-effects.

However, pathologic states are being discussed as well, wherein apoptosis has negative effects and for the treatment of which apoptosis should be inhibited.

An example of such a disease is arteriosclerosis. In particular, the inventors were earlier able to show that particularly in the area of the arteriosclerotic plaques, apoptotic cells (particularly endothelial cells, smooth muscle cells) come up and that such coming up is amplified by disturbed flow conditions, i.e. is flow-dependent (Freyberg et al., BBRC, 286, 141-149, 2001). Furthermore, the inventors could show that substances inhibiting the binding of TSP-1 to IAP and/or $\alpha_v\beta_3$ can also inhibit flow-dependent apoptosis.

Further diseases discussed in connection with increased up-coming apoptosis are AIDS and Alzheimer's disease.

Also in wound healing, apoptosis of participating cells such as fibroblasts, muscle cells and endothelial cells, plays a significant role. Inhibition of apoptosis should, therefore have a favorable influence on wound healing.

SUMMARY

There exists, therefore, a high need for substances having a positive or a negative influence on apoptosis. In particular, it would be favorable to be able to inhibit apoptosis which is flow-dependent and causally related to arteriosclerosis. There is, furthermore, a high need for pharmaceutical formulations comprising substances that can be used for treating states wherein inhibition or induction of apoptosis is indicated, particularly for the treatment of arteriosclerosis, but also of AIDS. Alzheimer's disease and cancer. In this connection, such substances should, if possible, be of lowest molecular weight and/or be small peptides in order to ensure good biological availability.

Therefore, the disclosure provides apoptotically active substances, preferably peptides. In particular, the disclosure provides substances, preferably peptides, which can inhibit flow-dependent apoptosis of the endothelial cells induced by TSP-1. The disclosure further provides pharmaceutical preparations by which diseases such as AIDS, Alzheimer's disease, cancer and wound healing disorders can be treated where inhibition or induction of apoptosis is indicated.

These, and further objects not explicitly referred to which however can without any difficulties be taken from the preceding appreciation of the prior art will be solved by the exemplified embodiments of the present invention defined in the claims.

DETAILED DESCRIPTION

The disclosure particularly makes available substances comprising peptides having one of the amino acid sequences represented in SEQ ID NOs 1 through 19.

In a preferred exemplified embodiment, apoptosis-inhibiting substances are concerned comprising amino acid sequences of the general formula (1):

$$R\text{-}A_1\text{-}Y\text{-}V\text{-}V\text{-}M, \quad\quad (\text{SEQ ID NO. 20})$$

wherein $A_1$ stands for A, D, E, G, M, N, T, W or Y, or pharmaceutically acceptable salts of these substances.

In a further preferred exemplified embodiment, apoptosis-inducing substances are concerned comprising amino acid sequences of the general formula (2)

$$R\text{-}A_2\text{-}Y\text{-}V\text{-}V\text{-}A_3, \quad\quad (\text{SEQ ID NO. 21})$$

wherein $A_2$ stands for A, L, P, S or C and $A_3$, if $A_2$ stands for A, is A and if $A_2$ stands for L, P, S or C, is M, or pharmaceutically acceptable salts of these substances.

Further particularly preferred embodiments comprise amino acid sequences shown in SEQ ID NOs 12, 18 and 19.

For the purposes of the disclosure, the internationally-common one-letter code for amino acids is used; i.e. A stands for alanine (Ala), C for cysteine (Cys), D for asparagine acid (Asp), E for glutaminic acid (Glu), F for phenyl alanine (Phe), G for glycine (Gly), L for leucine (Leu), M for methionine (Met), N for asparagine (Asn), P for prolin (Pro), R for arginine (Arg), S for serine (Ser), T for threonine (Thr), V for valine (Val), W for tryptophane (Trp) and Y for tyrosine (Tyr). In this connection, L-amino acids are represented by capital letters and D-amino acids by using small letters.

In accordance with a particularly preferred aspect, the disclosure relates, therefore, to apoptosis-inhibiting substances, preferably proteins or peptides comprising one of the peptide sequences shown sub SEQ ID NO 1 through SEQ ID NO 11, or the corresponding pharmaceutically acceptable salts thereof.

In accordance with a further particularly preferred aspect, the disclosure relates also to apoptosis-inducing substances, preferably proteins or peptides comprising one of the peptide sequences shown sub SEQ ID NO 12 through SEQ ID NO 19, or the corresponding pharmaceutically acceptable salts thereof.

Furthermore, the disclosure relates to the use of disclosed substances, preferably proteins or peptides comprising at least one of the amino acid sequence shown in SEQ ID NO 1 through SEQ ID NO 11, for the production of pharmaceuticals, particularly for the production of pharmaceuticals for the treatment of arteriosclerosis, AIDS and Alzheimer's disease and, particularly preferred in this connection, of arteriosclerosis.

The disclosure relates, furthermore, to the use of disclosed peptides comprising at least one of the amino acid sequence shown in SEQ ID NO 12 through SEQ ID NO 19, for the production of pharmaceuticals, particularly for the production of pharmaceuticals wherein the death of cells should be caused, for instance for the treatment of cancer.

Surprisingly, peptides comprising an amino acid sequence shown by formula (1) inhibit apoptosis at an extremely strong measure. In particular, these peptides are outstandingly suited to inhibit flow-dependent TSP-1-induced apoptosis of endothelial cells. It is assumed, however, that these peptides are also able to inhibit apoptosis in other cells.

As particularly preferred exemplified embodiments, the following peptides/peptide sequences are made available:

| | | |
|---|---|---|
| 1. | R-A-Y-V-V-M | (SEQ ID NO 1) |
| 2. | R-W-Y-V-V-M | (SEQ ID NO 2) |
| 3. | R-Y-Y-V-V-M | (SEQ ID NO 3) |
| 4. | R-E-Y-V-V-M | (SEQ ID NO 4) |
| 5. | K-R-A-Y-V-V-M-W-K-K | (SEQ ID NO 5) |
| 6. | K-R-E-Y-V-V-M-W-K-K | (SEQ ID NO 6) |
| 7. | R-G-Y-V-V-M | (SEQ ID NO 7) |
| 8. | R-M-Y-V-V-M | (SEQ ID NO 8) |
| 9. | R-T-Y-V-V-M | (SEQ ID NO 9) |
| 10. | R-N-Y-V-V-M | (SEQ ID NO 10) |
| 11. | R-D-Y-V-V-M | (SEQ ID NO 11) |
| 12. | M-V-V-Y-F-R | (SEQ ID NO 12) |
| 13. | R-A-Y-V-V-A | (SEQ ID NO 13) |
| 14. | R-L-Y-V-V-M | (SEQ ID NO 14) |
| 15. | R-P-Y-V-V-M | (SEQ ID NO 15) |
| 16. | R-S-Y-V-V-M | (SEQ ID NO 16) |
| 17. | R-C-Y-V-V-M | (SEQ ID NO 17) |
| 18. | m-v-v-y-f-r | (SEQ ID NO 18) |
| 19. | m-v-v-y-a-r | (SEQ ID NO 19) |

For the purposes of the disclosure, there is understood under the term "peptide" a substance consisting of a chain of two or more amino acids bound by peptide bonds. In particular, apoptotically active peptides according to the invention have a chain length of <100 amino acids, preferably of <75, particularly preferred of <50, more particularly preferred of <25 and most preferred of <15 amino acids.

Particularly preferred for the purposes according to the disclosure are, therefore, peptides which comprise one of SEQ ID NOs 1 through 19 and comprise either at the N-terminal and/or the C-terminal end one to three additional amino acids each.

For the purposes of the disclosure, the term "protein" will mark a substance in which a plurality of "peptides" are bonded with one another, for instance by molecular bonds, such as disulfide bridges or by salt bridges. This definition covers simultaneously both native proteins and at least partly "artificial" proteins, while such "artificial" proteins can be altered, for instance by added chemical residues to the amino acid chain which do not occur in native proteins.

For the purposes of the disclosure, the term "apoptotically active" will mean that the addition of the respective substance to the test system shown in Examples 5 and 6 generates either a positive or negative inhibition index. Particularly endothelial cells, preferably especially HUVEC, are to this end cultivated in a medium which includes 1 µg TSP-1 per ml. The percentage apoptosis values of such positive control will then serve, as shown in the examples, for the calculation of the inhibition index for those substances which are used as potential inhibitors together with the inductor TSP-1 in parallel tests. A negative control shows the absence of any other inductors.

A positive inhibition index shows in this connection that the respective substance inhibits apoptosis. A negative inhibition index shows in this connection that the used substance induces apoptosis, i.e. amplifies the TSP-1-induced apoptosis.

Negative peptides, though, often show lower metabolic stability vis-a-vis peptidases and relatively small biological availability.

Starting from the above-shown peptides, one skilled in the art can without employing inventive activity develop quite a series of deducted compounds which have a similar or equal mode of action and which are also referred to, inter alia, as peptide mimetics.

For the purposes of the disclosure, peptide mimetics will, in this connection, denote compounds which imitate the structure of peptides and, as ligands, are able to either imitate (agonist) or block (antagonist) the biological activity on the receptor/enzyme level. The peptide mimetics should in particular provide for improved biological availability and improved metabolic stability. The kind of mimetization may extend from the lightly changed starting structure up to the pure non-peptide. See, for instance, A. Adang et al.[.], Recl. Trav. Chim. Pays-Bas 113 (1994), 63-78.

In principle, the following possibilities for mimetization/derivatization of a peptide structure are available:
Use of D- instead of L-amino acids
Modification of the side chain of amino acids
Alteration/lengthening of the peptide main chain
Cyclization for conformation stabilization
Use of templates enforcing a particular secondary structure
Use of a non-peptidic backbone which imitates together with suitable residues/side chains the structure of the peptide.

While the proteolytic stability of a peptide can be increased by exchanging against D-amino acids, the modification of the side chains of one of the amino acids often leads to an improvement of the bonding properties of the whole peptide.

When changing the peptide backbone, an exchange of an amid group against amid-like groupings occurs as a rule (J. Gante, Angew. Chem. 106 (1994), 1780-1802). By these measures, both bonding affinity and metabolic stability of the native peptide can be influenced.

By cyclization of a linear peptide the flexibility thereof and hence its global conformation is fixed. When fixing the biologically active conformation, the affinity of the peptide relative to the receptor is increased since entropy decrease when bonding is smaller than when bonding a flexible linear peptide. To this end, amino acid side chains which do not take part in receptor recognition are connected with one another or with the peptide skeleton.

The secondary structure of the peptide plays a decisive role for the molecular recognition of the receptor. In addition to α-helix and β-pleated sheet, so-called turns constitute significant conformation elements as turning points in the peptide chain. The replacement of these structural units by an element which stabilizes after the insertion into a peptide a defined secondary structure, has led to the concept of the secondary structure mimetic.

The water solubility, too, of the peptides can be increased for instance by the introduction of S- and C-glycopeptide derivatives. Further measures may for instance include polyethylene glycolization of the peptides.

Lipophilicity of the hexapeptides may be increased as well in that for instance phenyl alanines are attached to the peptide sequence.

Cyclization and N-terminal modification of peptides has for instance been described by Borchard, Journal of controlled Release 62 (1999), 231-238, and by Blackwell et al., J. Org. Chem. 10 (2001), 5291-302.

It is, therefore, obvious that one skilled in the art starting from the knowledge imparted by the disclosure will easily arrive at quite a series of deducted peptide mimetics which, however, are all covered by the scope of the disclosure.

Under a further preferred aspect, the disclosure provides also for peptide mimetics which have been deducted from SEQ ID NOs 1 through 19 and for substances comprising such peptide mimetics.

In particular, the disclosure provides, under a further preferred aspect, the use of peptide mimetics deducted from SEQ ID NOs 1 through 11 and of substances comprising such peptide mimetics for the production of a pharmaceutical for treating arteriosclerosis, AIDS and Alzheimer's disease and, in this connection, with preference of arteriosclerosis.

In particular, the disclosure provides, under a further preferred aspect, the use of peptide mimetics deducted from SEQ ID NOs 12 through 19 and substances comprising such peptide mimetics for the production of a pharmaceutical for cancer treatment.

Under a further preferred aspect of the disclosure, such peptides, or correspondingly derivatized peptides, respectively, can also be used as diagnostic reagents. The substances of the disclosure, preferably the peptides of SEQ ID NOs 1 through 19, bind to apoptotic cells and can, therefore, outstandingly be used as a diagnosis tool, for instance to prove the existence of apoptotic cells in the area of arteriosclerotic lesions and hence lesions as such. To this end, the substances are labeled. For such labeling, one skilled in the art is aware of a plurality of methods which can be selected according to the purpose of use.

Suitable methods have for instance been described in U.S. Pat. No. 4,479,930 (Hnatovich), U.S. Pat. No. 4,652,440 (Paik et al.), and U.S. Pat. No. 4,668,503 (Hnatowich).

For the purposes of the disclosure, the term "labeled substance according to the disclosure" denotes any substance of the disclosure which includes labeling substances known from the prior art and used as a standard for labeling peptides, such as general radio isotopes such as for instance rhenium or technetium, but also enzymes, enzyme substrates, antibodies, epitopes for the recognition on specific antibodies/fragments etc. One skilled in the a very easily recognize to above enumeration as exemplary and not conclusive.

If the substances according to the disclosure are to be used as diagnosis tool, any labeling method known in the prior art can be used.

Substances according to the i disclosure which constitute active components of a pharmaceutical preparation are, in general, dissolved in a pharmaceutically acceptable carrier. Examples of pharmaceutically acceptable carriers may include buffer solutions such as phosphate buffer or citrate buffer. In order to maintain the activity of the peptides, reagents may also be added which are pharmaceutically acceptable maintaining, for instance, a reducing environment in the pharmaceutical preparation.

The specific dosage and posology depends for each patient on a number of factors including the activity of the used specific compounds, the patient's age, the body weight, the general health status, the gender, nutrition, time of the administration, way of administration, the excretion rate, the combination with other pharmaceuticals and the severity of the individual disease to which the therapy is applied. Depending on these factors, it is determined by a physician.

Normally, peptide pharmaceuticals are parenterally administered, for instance by an inhalation spray, rectally, by subcutaneous, intravenous, intramuscular, intra-articular and intrathecal injection and infusion techniques, or externally in pharmaceutical formulations which include conventional pharmaceutically acceptable carriers, adjuvants and vehicles. Depending on the kind of the identified substance, other ways of administration, oral for instance, can be considered as well. In wound healing, the identificates according to the disclosure are preferably administered in the form of ointments or powder.

The disclosure also provides for pharmaceutical compositions which comprise an active amount of an apoptotically active substance, preferably a peptide, a protein or peptide mimetic in combination with a conventional pharmaceutical carrier. A pharmaceutical carrier is for instance a solid or liquid filler, an encapsulation material or a solvent. Examples of materials which can serve as pharmaceutical carriers include sugars, such as lactose, glucose and saccharose; starch such as maize starch and potato starch, cellulose and the derivatives thereof, such as sodium carboxymethyl cellulose, ethylcellulose and cellulose acetate; pulverized tragacanth; malt, gelatin, tallow; pharmaceutical carriers such as cocoa butter and suppository wax; oils such as peanut oil, cotton seed oil, carthamus oil, sesame oil, olive oil, maize oil, soy bean oil; polyalcohols, such as propylene glycol, glycerin, sorbitol, mannitol and polyethylene glycol; esters, such as ethyl oleate and ethyl laureate; agar, buffer means, such as magnesium hydroxide and aluminum hydroxide; alginic acid; pyrogenically-free water; isotonic salt solution; Ringer's solution, ethyl alcohol and phosphate buffer solutions, as well as other non-toxic compatible substances which are used in pharmaceutical formulations. Wetting agents, emulgators and lubricating agents, such as sodium lauryl sulfate and magnesium stearate, also coloring agents, coating agents and perfuming agents and preserving agents can be present in the preparations as well, corresponding to the galenic specialist's request. The amount of the active agent which is combined with the carrier materials in order to produce an individual dose will vary depending on the patient to be treated and the particular method of administration.

Pharmaceutically acceptable salts of the substances according to the disclosure, preferably peptides, proteins or peptide mimetics can be produced in a well known way, for instance by dissolving the compounds of the invention in the corresponding diluted acid or base, e.g. hydrochloric acid or sodium hydroxide solution, and subsequently freeze-drying them. Metal salts can be obtained by dissolving the compounds according to the disclosure in solutions which contain the corresponding ion, and subsequently isolating the compound via HPLC or gel permeation processes.

The following examples will explain the disclosure in more detail:

EXAMPLE 1

Cultivation of Human Umbilical Vein Endothelial Cells (HUVEC)

Solutions (Sterile):
Culture medium: IF basal medium+15% (v/v) NCS; 5 µg/ml transferrin, 5 µg/ml heparin, 0.7 µg/ml FGF, 2 mM L-glutamine [IF basal medium: 1:1 mixture of Iscove's Modified Dulbecco's Medium (IMDM) and Ham's F12, both produced by Life Technologies, Paisley (England)]
NCS: Newly-born calves serum (Sebak, Aidenbach)
FGF: Fibroblast growth factor (own production, purified from pig brain).
Materials:
  Cell culture vessels, gelatinized
Procedure:
  Cultivation of HUVEC takes place in gelatin-coated culture vessels at 37° C., 5% $CO_2$ and water vapor saturated atmosphere. The culture medium is exchanged every two to three days; in case of confluence, the cells are passaged at a cleavage rate of from 1:3 to 1:5. HUVEC grow strictly contact-inhibited and form unilaminar cell bed having the typical cobble-stone morphology. In case of confluence, the cultures reach cell densities of $4$-$9 \times 10^4$ cells/cm$^2$. For apoptosis examinations, HUVEC cultures of passages 1-4 are exclusively employed.
Coating of Culture Vessels:
Solutions (Sterile):
Gelatin solution, 1% (w/v) in milli-Q-water
Suspend 1 g gelatin (cell culture tested) in 100 ml milli-Q-water, dissolve by autoclaving for 20 minutes at 121° C. and 2 bars, and store at room temperature.
PBS (140 mM NaCl, 3 mM KCl, 8 mM $Na_2HPO_4$, 1.5 mM $KH_2PO_4$)
8 g/l NaCl
0.2 g/l KCl
1.44 g/l $Na_2PO_4 \times 2\ H_2O$
0.2 g/l $KH_2PO_4$
Dissolve the salts in a corresponding volume of milli-Q-water, autoclave for 20 minutes at 121° C. and 2 bars, and store at room temperature. The pH value is controlled and is between 7.2 and 7.4.
Materials:
  Cell culture vessels
Procedure:
  For the cultivation of adherently growing cells, culture vessels are coated with gelatin. The bottom of the cell culture vessels is covered with sterile gelatin solution, the cell culture vessels are maintained for 15 minutes at room temperature. The gelatin solution is sucked off, the cell culture vessels are once washed with PBS and in such a state can be used.
Subcultivation of Adherent Cells
Solutions (Sterile):
PBS
Trypsin/EDTA solution
Dissolve 0.05% (w/v) trypsin and 0.02 (w/v)EDTA in PBS and filter aseptically.
Materials:
  Cell culture vessels, gelatinized
Procedure:
  The cells are detached with a Trypsin/EDTA solution from the culture vessel. The culture medium is sucked off, the bottom of the culture vessel is shortly washed with PBS and covered with Trypsin/EDTA solution (~1 ml for a culture face of 25 cm$^2$). The enzyme solution is immediately sucked off again so that a thin liquid film remains on the cells. The cells are maintained for one minute to ten minutes at room temperature and the detachment of the cells is observed under the microscope. Detachment of the cells can be accelerated by gently pounding the culture vessel at the edge. The cells are received in a fresh culture medium, possibly counted, and seeded in new culture vessels.

EXAMPLE 2

Determination of the Apoptosis Rate by Dyeing Apoptotic Cells with DAPI

DAPI belongs to the indole dye stuff group and is a selective DNS dye stuff. The dye stuff is activated et 340-360 nm, and the emission maximum is at about 480 nm. It is used for apoptosis examinations [compare Cohen et al. Immunology Today, 14. No. 3, 126-130 (1993)]
Morphologic Evaluation:
Solutions:
PBS
Formaldehyde solution
4% (v/v) formaldehyde in PBS
DAPI solution (Molecular Probes, Leiden, Netherlands)
2 µg/ml DAPI in methanol
Materials:
  Petri dish (35 mm) with cells in culture
Procedure:
  The culture supernatant of a Petri dish is sucked off, the cell bed is fixed on ice for 15 minutes with 1 ml formaldehyde solution, is washed twice with 2 ml PBS, is added 0.5 ml DAPI solution for 15 minutes, is washed with PBS and evaluated under the fluorescence microscope. A UV filter set and a 20× and a 40× objective are used. 500 to 1000 cells are selected at random and the cells having apoptotic nuclei are counted.

The apoptosis index is calculated in accordance with the following formula:

$$\text{Apoptosis index [\%]} = \text{number of apoptotic cells/total cell number} \times 100$$

Flow Cytometry:
Solutions:
PBS
Medium
Ethanol (reagent-grade) ice-cooled (−20° C.)
DAPI buffer
DAPI stock solution
DAPI dye solution Procedure:

The culture supernatant is sucked off and the cells are trypsinized without washing them with PBS. The cell suspension is received in medium, is counted, is centrifuged at 800×g for 5 minutes, the sediment is re-suspended in 0.5 ml IF and is dripped into 1.5 ml ice-cold ethanol. The suspension is stored overnight at 20° C. After renewed centrifugation and re-suspending of the sediment in 2 ml PBS, there follows a half-hour incubation at 37° C., further centrifugation, re-suspending of the sediment in 5 ml DAPI solution, and counting in the flow cytometer at a counting rate of 50 to 300 events per second. The coating obtained shows a high peak of cells in the G phase of the cell cycle, followed by a fraction of cells in the S phase (medium fluorescence intensities) and a last peak of high fluorescence intensities representing the cells in the $G_2$ phase. Caused by the decreasing absolute DNS amount per cell, apoptotic cells appear in a sub-$G_1$ peak [Darzynklewicz Z. et al., Cytometry, 13, 795-808 (1992); Zamai L. et al., Cytometry, 14, 891-897 (1993)]. This shows the appearance of an apoptosis under the selected conditions.

EXAMPLE 3

Induction of Apoptosis and Test System for Apoptotically Active Peptides or Proteins in Case of Cultivated Endothelial Cells The cells are cultivated as described in Example 1. Having obtained complete confluence, the cells are used for the test. First, thrombospondin 1 (1 μg/ml) is added to fresh medium and compared to the effect of fresh medium on the apoptosis rate of HUVEC. Table 1 shows that the addition of thrombospondin leads to a significant increase of the apoptosis rate. The apoptosis observed while adding fresh medium is induced by the thrombospondin secreted during the course of the experiment.

TABLE 1

Induction of apoptosis at HUVEC with TSP-1

| Culture medium | Apoptosis rate (%) after 24 h |
|---|---|
| Fresh medium | 0.9 ± 0.1 |
| Fresh + TSP-1 (1 μg/ml) | 3.0 ± 0.4 |

EXAMPLE 4

Peptide Synthesis

The peptides used were synthetisized by the NMI (Naturwissenschaftliches und Medizinisches Institut an der Universität Tuebingen, Reutlingen, Germany) based on data provided by Cyto Tools.

EXAMPLE 5

Identification of Apoptotically Active Hexamer Peptides Based on the Process According to the Disclosure The cells were cultivated as described in Example 1. The cells are seeded in the corresponding culture vessels (e.g. 24-hole plate/0.5 ml per cavity) and, having obtained complete confluence, are employed for the test. The cells are provided with new medium:

(a) fresh culture medium [Base rate of apoptosis],
(b) fresh medium with 1 μg/ml TSP-1 [Apoptosis-induced substance; control],
(c) medium (b)+peptide of SEQ ID NO 1, 1 mM
(d) medium (b)+peptide of SEQ ID NO 2, 1 mM
(e) medium (b)+peptide of SEQ ID NO 3, 1 mM
(f) medium (b)+peptide of SEQ ID NO 4, 1 mM
(g) medium (b)+peptide of SEQ ID NO 7, 1 mM
(h) medium (b)+peptide of SEQ ID NO 8, 1 mM
(i) medium (b)+peptide of SEQ ID NO 9, 1 mM
(j) medium (b)+peptide of SEQ ID NO 10, 1 mM
(k) medium (b)+peptide of SEQ ID NO 11, 1 mM
(l) medium (b)+peptide of SEQ ID NO 12, 1 mM
(m) medium (b)+peptide of SEQ ID NO 13, 1 mM
(n) medium (b)+peptide of SEQ ID NO 14, 1 mM
(o) medium (b)+peptide of SEQ ID NO 15, 1 mM
(p) medium (b)+peptide of SEQ ID NO 16, 1 mM
(q) medium (b)+peptide of SEQ ID NO 17, 1 mM
(r) medium (b)+peptide of SEQ ID NO 18, 1 mM
(s) medium (b)+peptide of SEQ ID NO 19, 1 mM After 24 hours of incubation under culture conditions (Example 1), the cells are fixed, dyed with DAPI and morphologically examined under the fluorescence microscope, or flow-cytometrically examined, respectively. The apoptotic cells and the total number are determined and the apoptosis index is calculated (percentage of apoptotic cells). The data of three independent experiments giving the mean values and the standard deviation are given in Table 2. Inhibitorically active peptides show, in accordance with the disclosure, a positive inhibition index while inductory peptides show, in accordance with the disclosure, a negative inhibition index.

TABLE 2

The following peptides are tested:

| SEQ ID NO | Amino acid sequence | Apoptosis index [%] | Inhibition index [%]* |
|---|---|---|---|
| K | Control | 3.28 ± 0.55 | |
| (1) | R-A-Y-V-V-M | 0.83 ± 0.24 | +75.3 ± 7.5 |
| (2) | R-W-Y-V-V-M | 1.30 ± 0.26 | +61.9 ± 7.7 |
| (3) | R-Y-Y-V-V-M | 0.85 ± 0.17 | +74.7 ± 5.0 |
| (4) | R-E-Y-V-V-M | 1.04 ± 0.30 | +69.0 ± 8.9 |
| (7) | R-G-Y-V-V-M | 1.83 ± 0.37 | +46.4 ± 11.1 |
| (8) | R-M-Y-V-V-M | 1.84 ± 0.39 | +44.2 ± 11.6 |
| (9) | R-T-Y-V-V-M | 1.86 ± 0.36 | +44.5 ± 9.8 |
| (10) | R-N-Y-V-V-M | 2.06 ± 0.53 | +39.5 ± 15.8 |
| (11) | R-D-Y-V-V-M | 2.12 ± 0.47 | +37.3 ± 14.0 |
| (12) | M-V-V-Y-F-R | 4.40 ± 0.53 | −34.1 ± 6.2 |
| (13) | R-A-Y-V-V-A | 4.98 ± 0.3 | −51.8 ± 6.0 |
| (14) | R-L-Y-V-V-M | 6.41 ± 0.63 | −95.4 ± 6.1 |
| (15) | R-P-Y-V-V-M | 5.67 ± 0.54 | −72.8 ± 6.4 |
| (16) | R-S-Y-V-V-M | 6.86 ± 0.37 | −108.4 ± 3.7 |
| (17) | R-C-Y-V-V-M | 13.97 ± 0.35 | −326.5 ± 3.6 |
| (18) | m-v-v-y-f-r | 14.6 ± 0.75 | −345.1 ± 5.1 |
| (19) | m-v-v-y-a-r | 11.4 ± 0.63 | −247.1 ± 5.4 |

*positive inhibition index = substance inhibited;
negative inhibition index = substance induced;

According to the disclosure, the inhibition index is calculated as follows:

inhibition index [%]=(measured apoptosis index•100/ apoptosis index control)−100

EXAMPLE 6

Improvement of the Inhibition Effect by Lengthening the Amino Acid Chain

Cell cultivation and the tests were carried out as described in Example 5. The peptides used are enumerated in Table 3.

TABLE 3

Results with lengthened peptide sequences

| SEQ ID NO | Amino acid sequence | Apoptosis index [%] | Inhibition index [%]* |
|---|---|---|---|
| | Control | 8.73 ± 0.43 | |
| (5) | K-R-A-Y-V-V-M-W-K-K | 0.37 ± 0.22 | +95.8 ± 2.6 |
| (6) | K-R-E-Y-V-V-M-W-K-K | 0.48 ± 0.22 | +94.5 ± 2.5 |

*positive inhibition index = substance inhibited;
negative inhibition index = substance induced

The invention claimed is:

1. Apoptotically active substance comprising a peptide having one of the amino acid sequences selected from the group consisting of M-V-V-Y-F-R (SEQ ID NO: 12), R-A-Y-V-V-A (SEQ ID NO: 13), R-L-Y-V-V-M (SEQ ID NO: 14), R-P-Y-V-V-M (SEQ ID NO: 15), R-S-Y-V-V-M (SEQ ID NO: 16), R-C-Y-V-V-M (SEQ ID NO: 17), m-v-v-y-f-r (D-amino acids) (SEQ ID NO: 18) and m-v-v-y-a-r (D-amino acids) (SEQ ID NO: 19), wherein the peptide induces apoptosis wherein the apoptotically active peptide has less than 15 amino acids.

2. Substance according to claim 1, which is labeled.

3. A pharmaceutical composition comprising a substance according to claim 1 or a pharmaceutically acceptable salt thereof and a pharmaceutically acceptable carrier.

4. Substance according to claim 1, wherein the peptide is SEQ ID NO: 18.

5. Substance according to claim 1, wherein the peptide is SEQ ID NO: 19.

* * * * *

```
                      SEQUENCE LISTING

<160> NUMBER OF SEQ ID NOS: 21

<210> SEQ ID NO 1
<211> LENGTH: 6
<212> TYPE: PRT
<213> ORGANISM: Artificial sequence
<220> FEATURE:
<223> OTHER INFORMATION: Synthetic peptide

<400> SEQUENCE: 1

Arg Ala Tyr Val Val Met
1               5

<210> SEQ ID NO 2
<211> LENGTH: 6
<212> TYPE: PRT
<213> ORGANISM: Artificial sequence
<220> FEATURE:
<223> OTHER INFORMATION: Synthetic peptide

<400> SEQUENCE: 2

Arg Trp Tyr Val Val Met
1               5

<210> SEQ ID NO 3
<211> LENGTH: 6
<212> TYPE: PRT
<213> ORGANISM: Artificial sequence
<220> FEATURE:
<223> OTHER INFORMATION: Synthetic peptide

<400> SEQUENCE: 3

Arg Tyr Tyr Val Val Met
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic peptide

<400> SEQUENCE: 4

Arg Glu Tyr Val Val Met
1               5

<210> SEQ ID NO 5
<211> LENGTH: 10
<212> TYPE: PRT
<213> ORGANISM: Artificial sequence
<220> FEATURE:
<223> OTHER INFORMATION: Synthetic peptide
```

```
<400> SEQUENCE: 5

Lys Arg Ala Tyr Val Val Met Trp Leu Leu
1               5                   10

<210> SEQ ID NO 6
<211> LENGTH: 10
<212> TYPE: PRT
<213> ORGANISM: Artificial sequence
<220> FEATURE:
<223> OTHER INFORMATION: Synthetic peptide

<400> SEQUENCE: 6

Leu Arg Glu Tyr Val Val Met Trp Lys Lys
1               5                   10

<210> SEQ ID NO 7
<211> LENGTH: 6
<212> TYPE: PRT
<213> ORGANISM: Artificial sequence
<220> FEATURE:
<223> OTHER INFORMATION: Synthetic peptide

<400> SEQUENCE: 7

Arg Gly Tyr Val Val Met
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic peptide

<400> SEQUENCE: 8

Arg Met Tyr Val Val Met
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic peptide

<400> SEQUENCE: 9

Arg Thr Tyr Val Val Met
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic peptide

<400> SEQUENCE: 10

Arg Asn Tyr Val Val Met
1               5

<210> SEQ ID NO 11
<211> LENGTH: 6
<212> TYPE: PRT
<213> ORGANISM: Artificial sequence
<220> FEATURE:
<223> OTHER INFORMATION: Synthetic peptide
```

```
<400> SEQUENCE: 11

Arg Asp Tyr Val Val Met
1               5

<210> SEQ ID NO 12
<211> LENGTH: 6
<212> TYPE: PRT
<213> ORGANISM: Artificial sequence
<220> FEATURE:
<223> OTHER INFORMATION: Synthetic peptide

<400> SEQUENCE: 12

Met Val Val Tyr Phe Arg
1               5

<210> SEQ ID NO 13
<211> LENGTH: 6
<212> TYPE: PRT
<213> ORGANISM: Artificial sequence
<220> FEATURE:
<223> OTHER INFORMATION: Synthetic peptide

<400> SEQUENCE: 13

Arg Ala Tyr Val Val Ala
1               5

<210> SEQ ID NO 14
<211> LENGTH: 6
<212> TYPE: PRT
<213> ORGANISM: Artificial sequence
<220> FEATURE:
<223> OTHER INFORMATION: Synthetic peptide

<400> SEQUENCE: 14

Arg Leu Tyr Val Val Met
1               5

<210> SEQ ID NO 15
<211> LENGTH: 6
<212> TYPE: PRT
<213> ORGANISM: Artificial sequence
<220> FEATURE:
<223> OTHER INFORMATION: Synthetic peptide

<400> SEQUENCE: 15

Arg Pro Tyr Val Val Met
1               5

<210> SEQ ID NO 16
<211> LENGTH: 6
<212> TYPE: PRT
<213> ORGANISM: Artificial sequence
<220> FEATURE:
<223> OTHER INFORMATION: Synthetic peptide

<400> SEQUENCE: 16

Arg Ser Tyr Val Val Met
1               5

<210> SEQ ID NO 17
<211> LENGTH: 6
<212> TYPE: PRT
<213> ORGANISM: Artificial sequence
<220> FEATURE:
<223> OTHER INFORMATION: Synthetic peptide

<400> SEQUENCE: 17
```

```
Arg Cys Tyr Val Val Met
1               5

<210> SEQ ID NO 18
<211> LENGTH: 6
<212> TYPE: PRT
<213> ORGANISM: Artificial sequence
<220> FEATURE:
<223> OTHER INFORMATION: Synthetic peptide

<400> SEQUENCE: 18

Met Val Val Tyr Phe Arg
1               5

<210> SEQ ID NO 19
<211> LENGTH: 6
<212> TYPE: PRT
<213> ORGANISM: Artificial sequence
<220> FEATURE:
<223> OTHER INFORMATION: Synthetic peptide

<400> SEQUENCE: 19

Met Val Val Tyr Ala Arg
1               5

<210> SEQ ID NO 20
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: Misc_feature
<222> LOCATION: (2)..(2)
<223> OTHER INFORMATION: Xaa=Ala, Asp, Glu, Met, Asn, Thr, Trp, or Tyr

<400> SEQUENCE: 20

Arg Xaa Tyr Val Val Met
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: Misc_feature
<222> LOCATION: (2)..(2)
<223> OTHER INFORMATION: Xaa=Ala, Leu, Pro, Ser, or Cys
<220> FEATURE:
<221> NAME/KEY: Misc_feature
<222> LOCATION: (6)..(6)
<223> OTHER INFORMATION: Xaa=Ala if residue 2 is Ala; Xaa=Met if residue
      2 is Leu, Pro, Ser, or Cys

<400> SEQUENCE: 21

Arg Xaa Tyr Val Val Xaa
1               5
```